(12) United States Patent
Levitt (10) Patent No.: US 12,128,147 B2
(45) Date of Patent: Oct. 29, 2024

(54) SHOPPING CART STERILIZATION SYSTEM AND METHOD

(71) Applicant: Jeffrey Levitt, San Diego, CA (US)

(72) Inventor: Jeffrey Marc Levitt, San Diego, CA (US)

( * ) Notice: Subject to any disclaimer, the term of this patent is extended or adjusted under 35 U.S.C. 154(b) by 708 days.

(21) Appl. No.: 17/369,591

(22) Filed: Jul. 7, 2021

(65) Prior Publication Data

US 2023/0011573 A1    Jan. 12, 2023

(51) Int. Cl.
*A61L 2/10* (2006.01)

(52) U.S. Cl.
CPC ............. *A61L 2/10* (2013.01); *A61L 2202/11* (2013.01); *A61L 2202/122* (2013.01)

(58) Field of Classification Search
CPC ... A61L 2/10; A61L 2202/11; A61L 2202/122
See application file for complete search history.

(56) References Cited

U.S. PATENT DOCUMENTS

2017/0340760 A1* 11/2017 Starkweather ............ A61L 2/10
2021/0369015 A1* 12/2021 Nevitt ....................... A61L 2/10

FOREIGN PATENT DOCUMENTS

KR       20200079358 A  *  7/2020

* cited by examiner

*Primary Examiner* — Sean E Conley
*Assistant Examiner* — Justin Hwang (57) ABSTRACT

A shopping cart sterilization system is provided comprising a sealable chamber with front and rear doors and a plurality of light arrays inside the chamber. The arrays comprise at least two horizontal fixtures attached along horizontal edges and at least one ultraviolet light bulb in each fixture for directing ultraviolet light at a cart in the chamber. The system also comprises a motor with pulleys and cables to move the arrays proximate and away from the cart. The system moves the light arrays proximate outer surfaces of the cart. Arrays are arranged in a basket arrangement for lowering into an internal area of the cart. Arrays are moved proximate a handle, a child seat, and wheels of the cart.

5 Claims, 7 Drawing Sheets

| ITEM NO. | QTY. | PART NAME |
|---|---|---|
| 1 | 1 | OUTER MODULAR CASING |
| 2 | 2 | 36 INCH ARRAY BRACKET |
| 3 | 12 | 36 INCH FIXTURE |
| 4 | 1 | LEFT SIDE CORD |
| 5 | 1 | RIGHT SIDE CORD |
| 6 | 2 | 24 INCH ARRAY BRACKET |
| 7 | 28 | 24 INCH FIXTURE |
| 8 | 1 | HANDLE SIDE CORD |
| 9 | 1 | BACK SIDE CORD |
| 10 | 2 | CENTER CORD |
| 11 | 8 | CURVED (+) HINGE |

SHOPPING CART STERILIZATION SYSTEM AND METHOD

CROSS REFERENCE TO RELATED APPLICATION

The present non-provisional patent application is related to U.S. Provisional Application No. 63/049,331 filed Jul. 8, 2020, the contents of which are incorporated herein in their entirety.

FIELD OF THE INVENTION

The present disclosure is in the field of public health and maintenance of sanitary conditions in public areas. More particularly, the present disclosure provides systems and methods of sterilizing shopping carts and similar devices by moving such carts into a specialized chamber and directing ultraviolet light from arrays of light fixtures placed proximate surfaces of the carts including internal surfaces of cart basket areas.

BACKGROUND

Carts used by the public for shopping, moving luggage at airports, and other purposes have long been known to have bacterial levels far greater than levels found in public restrooms. The number of bacteria detected on the shopping carts ranged from 110 to 11,000,000, and coliform bacteria from <3 to >7,259. Conforms were detected on 72% (61/85) of the carts sampled. Other studies have found the total quantity of heterotrophic bacteria are as great as $1.1 \times 10^7$ on handles and seats of shopping carts. Coliforms were detected on 72% of carts tested and E. coli was found on 51%.

Testing results stress the need for improved sanitation of shopping carts to reduce exposure to pathogens and potential transmission of microbial infections and the spread of viruses among the public. Recent public health problems including the spread of the Covid-19 virus highlighted this problem. Manual cleaning of these surfaces with wipes and chemical agents has proven to be inconsistent, labor intensive and unreliable.

DETAILED DESCRIPTION

Systems and methods described herein provide a sanitation chamber, machines and pulleys, and arrays of light fixtures containing ultraviolet light bulbs to sanitize shopping carts and other wheeled devices that accumulate pathogens as described above. The light fixtures are generally horizontal and connected to each other along their long or lengthwise edges. Each light fixture may contain two ultraviolet bulbs that when activated project ultraviolet light onto surfaces of a cart that has been rolled into and secured in the chamber.

Once the cart has been moved into the chamber, the machines and pulleys move the arrays into position near the various surfaces of the shopping cart. The system comprises arrays of various shapes and sizes that are configured for each surface of the cart. Separate arrays are provided to direct ultraviolet light at the handle, the child seat, and the wheels of the cart in addition to the flat horizontal or vertical surfaces of the general basket portion of the cart.

The system also provides for arrays to be arranged together in a box or basket structure that may then be lowered into the basket portion of the cart such that inside surfaces of the cart may be treated with ultraviolet light. Once the cart has been moved into position in the chamber, the machine, via pulleys, lowers the box structure into the basket of the cart and causes the ultraviolet bulbs to activate. All four inside surfaces The UVc-band of ultraviolet light provided herein is germicidal. The light's ability to destroy pathogens is related to the light's intensity, the light's distance from the surface being treated, and the duration of exposure. The systems provided herein project the UV light to within four centimeters of much of the surface of the cart or other object being treated, reducing the exposure time required for complete sterilization.

Systems and methods may provide a 4-log (99.99%) reduction of pathogens on cart surfaces. Current CDC standards for UV sterilization of medical equipment call for a 3-log (99.9%) reduction. Specific fluence necessary to destroy the Covid-19 virus has not yet been determined, but the projected 4-log reduction capability may allow for elimination of most pathogens.

The system includes conveyance hardware and controls that automate entry and exit of carts through the sanitation chamber. The system includes tracks on floor surfaces in front of, inside of, and exiting the sanitation chamber. Machinery inside the chamber and along the floor surfaces move the cart into and through the chamber.

The process of sanitation may be completed in under thirty seconds with the cart in a fixed position within the chamber. Larger, higher volume versions of the system may feature two or three chambers allowing for the sanitizing of multiple carts simultaneously. Single chamber machines may also be installed side-by-side to create multiple cart lanes to provide a range of installation options for those higher volume locations.

The system is modular in design and may be shipped "flat-packed" with final assembly completed at the on-site location. The design also allows the machine to be adapted for many types and sizes of shopping cart or for use sanitizing airport luggage carts, public strollers, or wheelchairs, as well as other objects. This design approach minimizes the number of parts to be required for manufacture, assembling, and servicing.

The system provides two different sizes of low-pressure mercury vapor tube-type ultraviolet bulbs. These bulbs may be 24" or 36" in length or may be of other length. In an embodiment, the bulbs may be:

36"—Osram #21283 G55T8/HO-83v, 55w. The 36" bulb may also be Philips #376343 or GE #15875.

24"—Philips #133405 F17T8/TUV—72v, 17w

The fixtures which house the bulbs hold two bulbs each. As noted, the fixtures are attached via their long horizontal sided to form arrays. The bulbs are controlled by rapid start electronic ballast with a high power-factor. This ballast type may satisfactorily suit the frequent cycling of the system as well as provide necessary light output without sacrificing lamp life.

Two types of fixtures are used throughout the system. They may be identical in design except for the fixture lengths (24" and 36"). The fixtures may taper from 5" wide to 2" at the back with 3.5" side walls, allowing the array to "flex" in either direction. Each fixture is designed to utilize two, T8-type tube lamps spaced 1" apart, with a single ballast to power the lamps. Fixtures are designed of molded, high impact plastic with open fronts, a protective grid and a parabolic reflector made of PTFE or another similar, highly reflective material to maximize UV levels. Subsequent designs may include similar single-lamp and/or three-lamp fixtures.

The fixtures are wired to be connected in series with a proprietary power cord and receptacle. The fixtures also have two physical hinge-like, pin-and-sleeve connectors along both front edge lengths (pins on one side, sleeves on the other) to allow for the fixtures to be physically attached to each other forming a light array, or be attached to fixed brackets within the sanitation chamber. The hinged connectors, as well as cabling guides on the back of the fixture, allows the arrays to be configured to accommodate many sizes and styles of shopping cart, as well as to be positioned and manipulated within the chamber at the beginning and end of the sanitizing cycle.

The light arrays allow for the bulbs to be in the closest proximity to the carts surfaces as possible to further increase the system's effectiveness and thus shorten cycle times. The light arrays are made by interconnecting multiple light fixtures to each other. The system may include seven arrays each comprised of three to six fixtures. Additional fixed-in-place fixtures installed within the sanitation chamber ensure sufficient UVc fluence (dosage) to all cart components including handles, child seat, basket, trolley, shelve and wheels.

A locking mechanism on the hinged connector between the fixtures allows for the array to be flat, curved or hang freely to adapt to any cart design and optimize array placement relative to the cart. Additionally, a simple "spacer" allows the distance between fixtures to be adjusted so arrays may be configured to accommodate most styles, sizes, or type of cart while optimizing the system's capabilities.

Within the sanitation chamber are two side fixture arrays, a basket array and a handle/seat array which are suspended from above with cable and pulleys allowing them to rest directly against the cart while sanitizing. The arrays may then be pulled out of the way to let the cart pass through the chamber after each cycle.

The front and rear arrays are mounted to brackets on the tilt-up entry and exit doors of the machine. Alternatively, the front and rear arrays may be suspended from above similar to the manner in which side arrays are provided. The lower array consists of two fixtures installed between the wheel tracks with additional fixtures along the outside of the wheel tracks to sanitize the cart's wheels and lower shelf.

The handle/seat array is directly connected to the rear array or may be suspended separately depending on the style of the cart the system is being configured to sanitize. This array can also be curved to allow it to wrap around or plunge into the handle and seat portion of the cart.

The basket array is a curved configuration of up to seven fixtures that is lowered into the cart basket at the start of each cycle in unison with the side arrays, as the entry and exit doors close.

The frame and outer casing are also modular in design. A simple curved tunnel with a footprint of under 4'×7', interlocking components expedites manufacturing and allows it to be flat-packed, shipped and easily deployed. Structural and framing components and guiderails are made from prefabricated aluminum and interconnect with a simple slip-lock mechanism. The outer casing is made from high-impact plastic designed to be branded for marketing and advertising and connects directly to the aluminum frame.

Tilt-up entry and exit doors integrate with the conveyance operation, may serve as mounting brackets for the front and rear light fixture arrays and seal the unit during the sanitation cycle to prevent any external UV exposure.

The system may be installed and operate as a free-standing unit. However, a through-the-wall installation may be placed at or near the store's entrance to serve as the primary pathway for carts to be brought inside the store. This method helps to ensure that only fully sanitized carts are being distributed to shoppers. Adapter kits may be provided for new construction and remodel installations.

Video screens may be available for an operator of the system to monitor progress of carts as they pass through the system. Other video screens may provide similar information as well as provide advertising for customers to view as they watch carts move in and out of the chamber.

Figure 1:
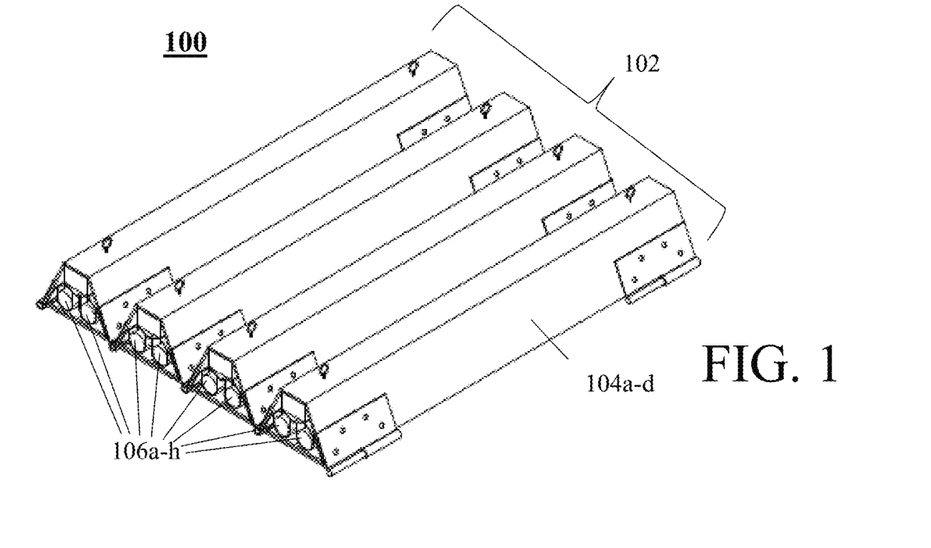
FIG. 1 is an image of an array according to an embodiment of the present disclosure.

Turning to the figures, FIG. 1 is an image of an array of a shopping cart sterilization according to an embodiment hereof. A system 100 is provided of shopping cart sterilization, the components of which are described above and below and depicted in the figures. FIG. 1 depicts an array 102 and quantity four of fixtures 104. Each of the four fixtures 104 contains quantity two of bulbs 106*a-h*. The bulbs 106*a-h* are ultraviolet and project light at surfaces of shopping carts as described herein.

Figure 2:
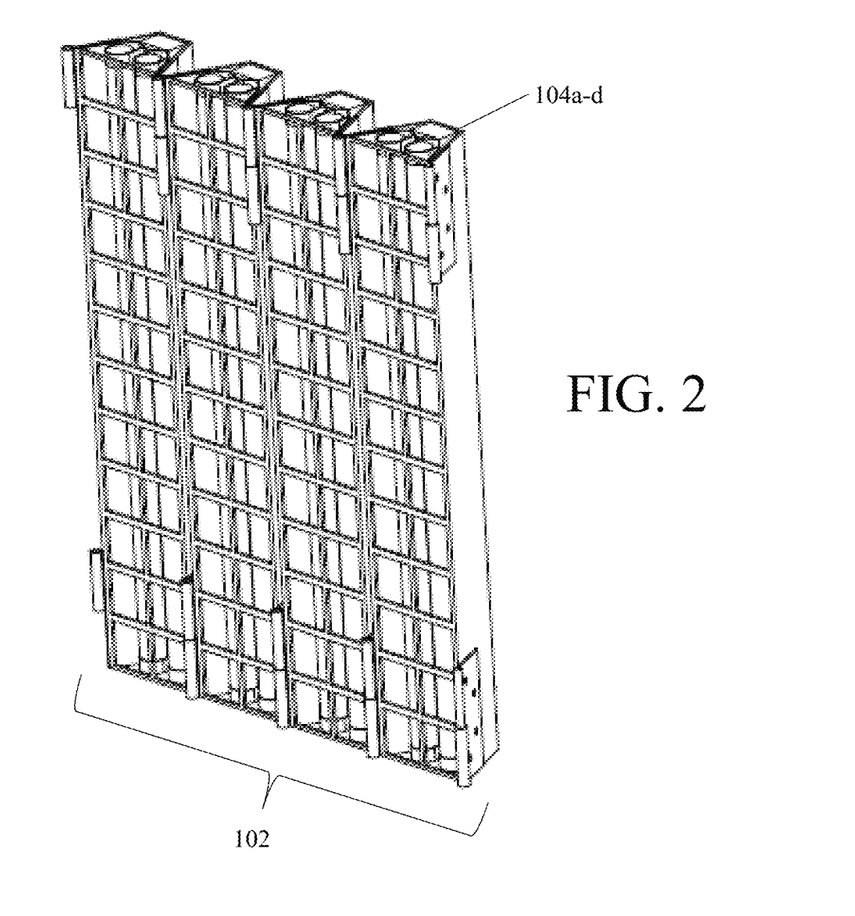
FIG. 2 is an image of an array according to an embodiment of the present disclosure.

FIG. 2 is an image of the array 102 and fixtures 104*a-d*. The full lengths of the bulbs 106*a-h* are shown. While the array 102 shown comprises four fixtures 104*a-d*, this depiction is for discussion purposes only. The array 102 may contain few than or more than four fixtures 104 in actual use.

Figure 3:
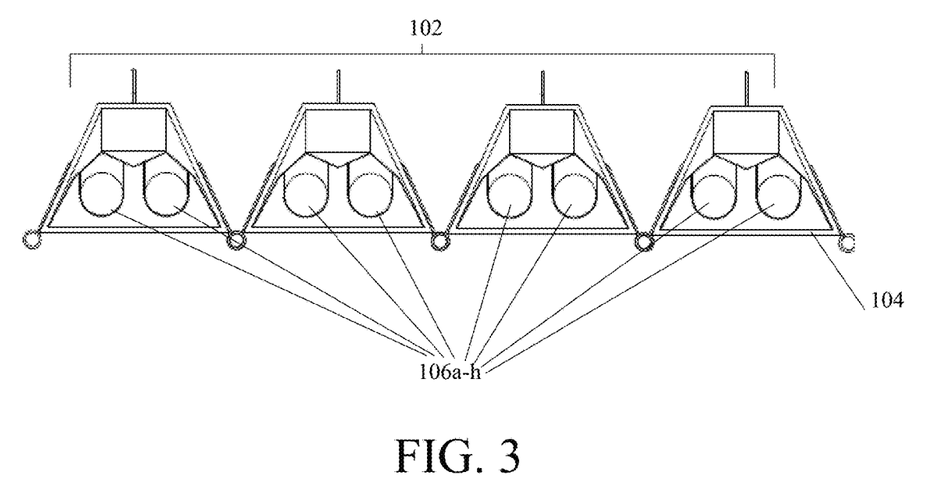
FIG. 3 is an image of an array according to an embodiment of the present disclosure.
Figure 4:
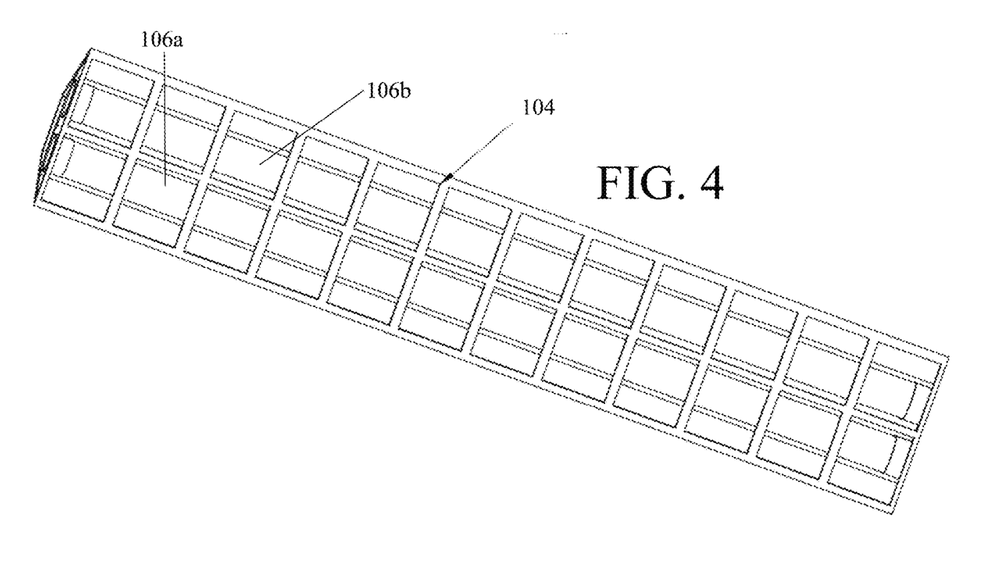
FIG. 4 is an image of a fixture according to an embodiment of the present disclosure.
Figure 5:
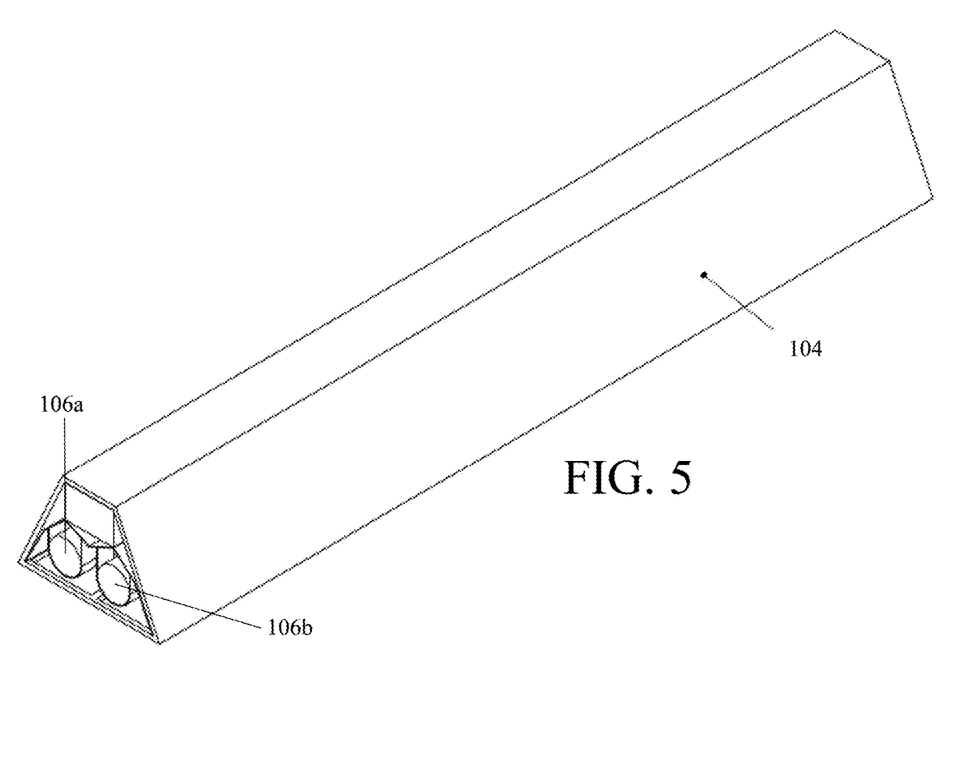
FIG. 5 is an image of a fixture according to an embodiment of the present disclosure.
Figure 6:
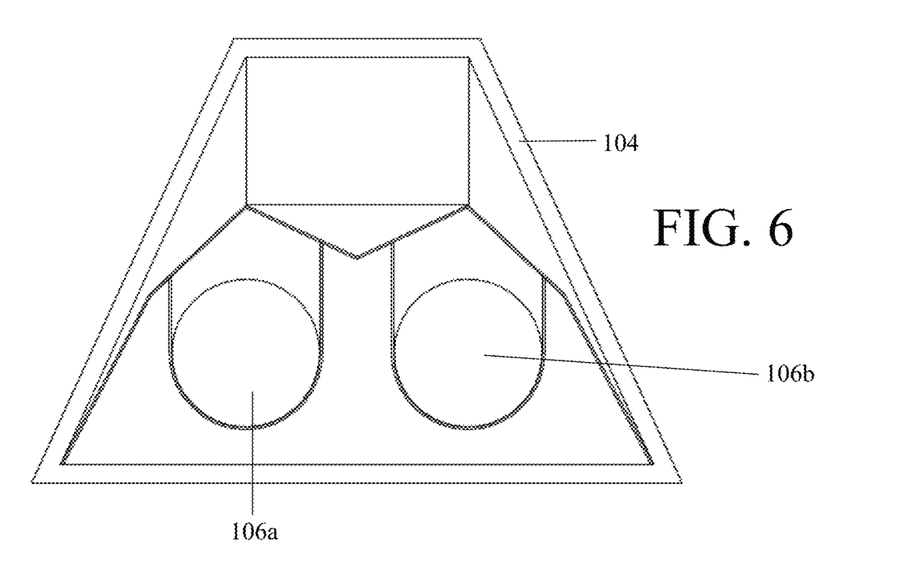
FIG. 6 is an image of a fixture according to an embodiment of the present disclosure.

FIG. 3 is an end view of the array 102. Four fixtures 104*a-d* are shown as are the eight bulbs 106*a-h*. FIG. 4, FIG. 5, and FIG. 6 are images of a single fixture 104 containing two bulbs 106*a-b*.

Figure 7:
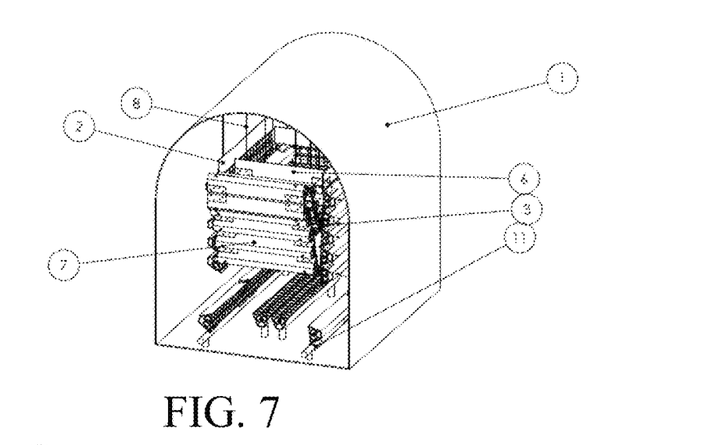
FIG. 7 is an image of a system of shopping cart sterilization according to an embodiment of the present disclosure.
Figure 8:
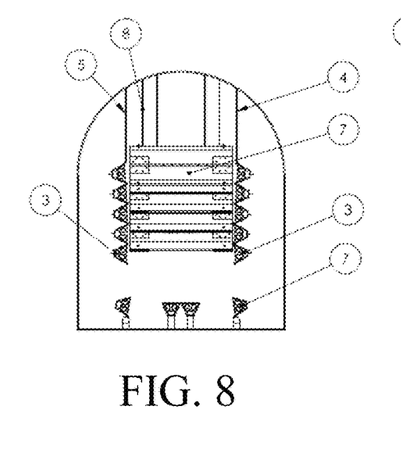
FIG. 8 is an image of a system of shopping cart sterilization according to an embodiment of the present disclosure.
Figure 9:
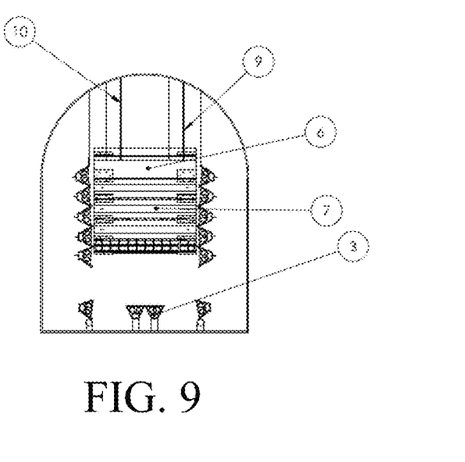
FIG. 9 is an image of a system of shopping cart sterilization according to an embodiment of the present disclosure.
Figure 10:
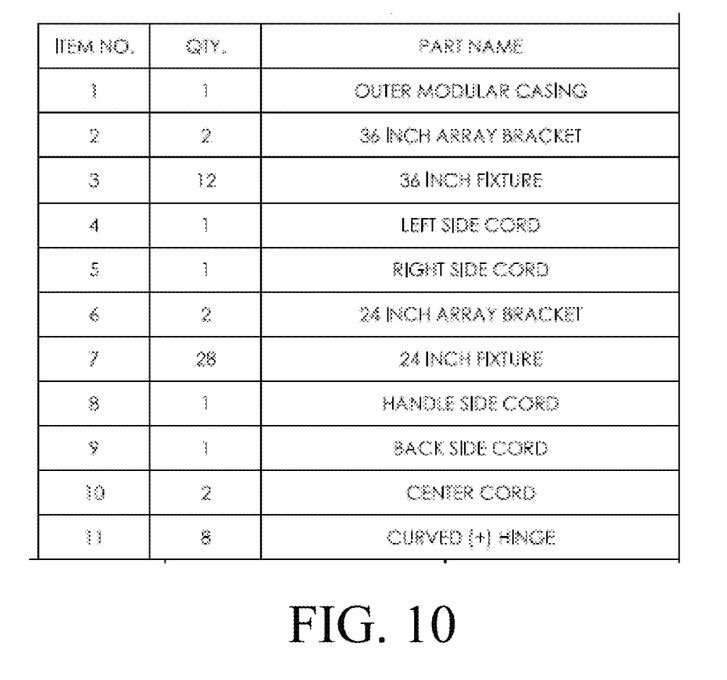
FIG. 10 is a table of part names for components depicted in FIG. 7-FIG. 9 according to an embodiment of the present disclosure.
Figure 11:
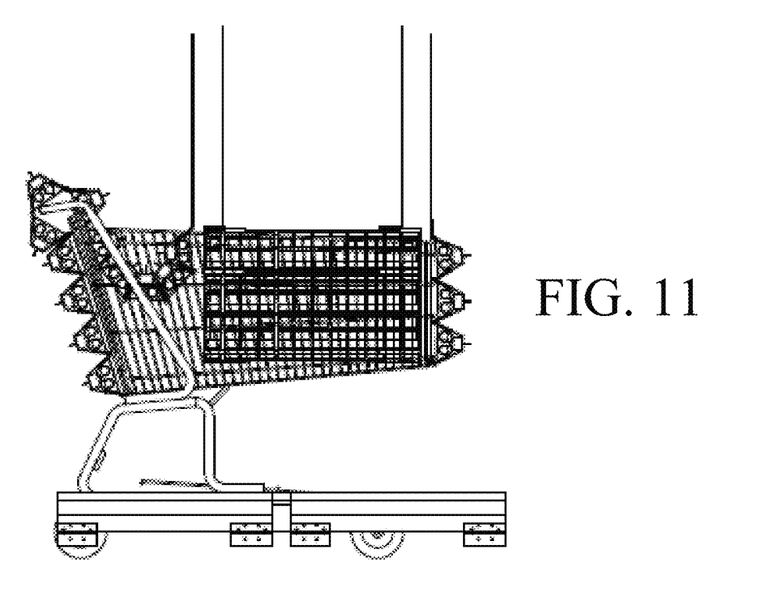
FIG. 11 is an image of a system of shopping cart sterilization depicted with sample shopping cart according to an embodiment of the present disclosure.
Figure 12:
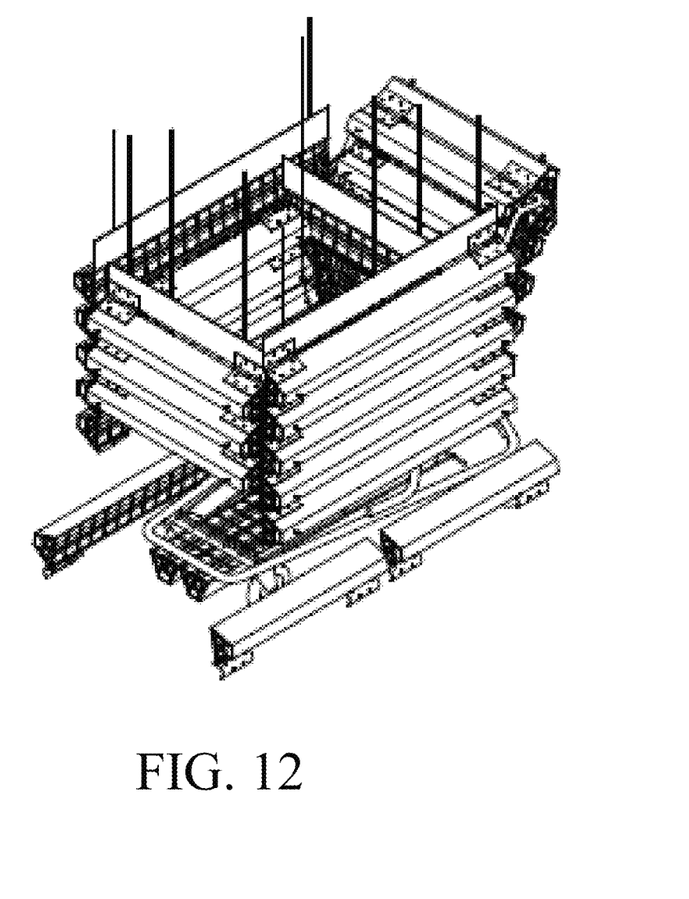
FIG. 12 is an image of a system of shopping cart sterilization depicted with sample shopping cart according to an embodiment of the present disclosure.

FIG. 7 through FIG. 9 are images of the entire system 100. Numbering and labeling for components shown in FIG. 7 through FIG. 9 is different from component numbering for FIG. 1 through FIG. 6 with numbering for FIG. 7 through FIG. 9 shown in a table in FIG. 10. The enclosure or chamber is shown in FIG. 7 through FIG. 9 as are the banks of arrays 102 connected in a box-like manner for lowering into the interior of the shopping cart. Also depicted are fixtures 104 on a floor area that direct ultraviolet light to wheel areas of a cart. FIG. 11 and FIG. 12 depict a shopping cart with arrays 102 in and around the cart. The arrays 102 may be lowered into place to treat the cart. In particular, a box-shaped set of arrays 102 is lowered into the basket area of the cart.

In embodiments, the system may be provided in several models. All may be built with the same primary modular components. Conveyance models are automated and continuous while sanitizing takes place with the cart in a fixed position within the chamber. In embodiments, some models may not provide conveyance such that carts must be manually pushed into the chamber and manually pulled out after sanitization.

One model is a pass-through conveyance tunnel that has a single chamber for cart sanitation. A second model is a dual chamber system intended for higher volume locations and is an extended version of the single chamber model. The second model operates much the same as the single chamber unit except two carts are serviced simultaneously.

A smaller form factor may be provided that is intended for locations with lower volume or for self-service installations. This model maintains the same sanitation capabilities and performance standards as larger units. The smaller model may be a manually operated, single-door cabinet with no conveyance mechanism. The operator would open the door, push the cart in, activate the machine, and remove a fully sanitized cart when the cycle ends.

Pass-through (non-manual) models are equipped with an automated conveyance system that feeds the carts into the machine, positions them within the sanitation chamber and pauses during the sanitizing cycle before ejecting them from the machine as the next cart loads into place.

The carts are guided and aligned by a series of railings and wheel tracks as they are pulled into and pushed through the chamber. The rear wheel tracks are inclined slightly until they pass through the sanitation chamber and then slope downward allowing gravity to help propel the carts out of the machine once sanitized.

A 110-volt AC powered, parallel shaft gear motor (for example Bison 100 Series or equivalent) paired with an ethernet-based programmable logic controller (for example Galil RIO-471xx PLC or equivalent) may provide for easy-to-use and cost-effective system control.

A listing of optional features follows:

Installation Kit—This kit is designed for conveyance models to allow for a through-the-wall retrofitted installation. It includes framing, seals, panels and hardware to facilitate incorporating and sealing the machine into the building.

Directional Exit Assembly—To accommodate many installation configurations, a mechanism is provided that directs the carts to the right or left as they exit the machine. This will allow the machine to be placed in a corner or to be utilized where space and fit may otherwise be a challenge.

Seat-Flap Sanitizer—To accommodate carts with integrated child seat flaps, a suction tube or mechanical device positions the flap allowing for thorough sanitizing of the entire seat area as well as both sides of the flap.

Heaters—An integrated heating unit maintains optimal operating temperatures for UV bulbs within the chamber. Cold climate optional auxiliary heaters may be added to maintain cycle times.

Cart Feeder—A cable feed assembly is available that is powered by the system's internal conveyor motor. The assembly works with the machine's conveyor and consists of a retractable cable with a handle or hook which pull carts onto the wheel tracks where the conveyance system then takes over. The cable port is located above the cart entry door, automatically retracts, and is controlled by the machine operator.

Truck-Mounted Service Kits—Adapter kits allow the system to be installed individually or two-abreast on a truck bed or inside a boxed truck with a rear door/ramp entry point and side exit. This truck mounted kit provides on-site servicing of customers that do not have a permanently installed machine at their location. This kit allows clients with multiple locations to independently establish their own cart sanitizing regimen.

Smart Controls/Operation—The system may be remotely monitored and controlled and may track, record, and transmit machine service alerts. The system may also provide marketing messages on display panels and compile individual cart usage data. This data can be utilized for service or billing, identifying individual cart service needs, and potentially be utilized for contact tracing and other purposes. The system may also have a keyed lock and require a physical key to activate operation.

Safeguards—Sensors and safety controls alert operators of any system or mechanical problems or service needs and terminate machine operation if necessary. Critical components and mechanical parts are monitored with sensors and control devices. Door closures, UV levels, operating temperature, lamp and ballast failure are all also continually monitored.

What is claimed is:

1. A shopping cart cleaning system, comprising:
an enclosure with front and rear doors;
floor tracks in front of and within the enclosure;
a plurality of horizontal light fixtures arranged in arrays;
a plurality of ultraviolet light bulbs contained in the fixtures;
motors and pulleys inside the enclosure that:
   raise and lower the arrays,
   move the arrays proximate a shopping cart contained within the enclosure for projection of ultraviolet light onto surfaces of the cart, and
   move the arrays away from the shopping cart upon completion of the projection of ultraviolet light;
conveyance hardware and controls that automate entry and exit of the carts through the enclosure; and
wherein some of the arrays are positioned in a basket arrangement for lowering into an internal area of the cart.

2. The system of claim 1, wherein some of the arrays are moved proximate a handle, a child seat, and wheels of the cart.

3. The system of claim 1, wherein the tracks promote movement of the cart into the enclosure and securing the cart in the enclosure while ultraviolet light is projected.

4. The system of claim 1, wherein the motor and pulleys are configurable to accommodate a plurality of sizes and shapes of carts.

5. The system of claim 1, wherein each of the front and rear doors has at least one array attached for projection of ultraviolet light on front and rear surfaces, respectively, of the cart.

* * * * *